US00PP32308P2

(12) United States Plant Patent
Contreras

(10) Patent No.: US PP32,308 P2
(45) Date of Patent: Oct. 13, 2020

(54) ***COTONEASTER* PLANT NAMED 'EMERALD BEAUTY'**

(50) Latin Name: ***Cotoneaster* x *suecicus***
Varietal Denomination: Emerald Beauty

(71) Applicant: Oregon State University, Corvallis, OR (US)

(72) Inventor: Ryan N. Contreras, Corvallis, OR (US)

(73) Assignee: Oregon State University, Corvallis, OR (US)

( * ) Notice: Subject to any disclaimer, the term of this patent is extended or adjusted under 35 U.S.C. 154(b) by 0 days.

(21) Appl. No.: 16/501,818

(22) Filed: Jun. 10, 2019

(51) Int. Cl.
*A01H 5/00* (2018.01)
*A01H 6/74* (2018.01)

(52) U.S. Cl.
USPC ..... Plt./226

(58) Field of Classification Search
USPC ..... Plt./226
See application file for complete search history.

(56) References Cited

PUBLICATIONS

Rothleutner et al., "Screening *Cotoneaster* for Resistance to Fire Blight by Artificial Inoculation," *HortScience,* 49, 1480-1485, 2014.

*Primary Examiner* — Susan McCormick Ewoldt
(74) *Attorney, Agent, or Firm* — Klarquist Sparkman, LLP

(57) ABSTRACT

'Emerald Beauty' is a new *Cotoneaster* cultivar with a compact, cushion-like to semi-rounded habit, dense foliage, and short internodes. It is novel for its combination of improved resistance to fire blight (*Erwinia amylovora*) and improved branching that requires little pruning in production or landscapes.

5 Drawing Sheets

STATEMENT OF GOVERNMENT SUPPORT

This invention was made with government support under 58-1230-3-501 awarded by the United States Department of Agriculture, Agricultural Research Service (USDA/ARS). The government has certain rights in the invention.

Botanical denomination: *Cotoneaster* x *suecicus.*

Variety designation: 'Emerald Beauty'.

BACKGROUND

The present invention relates to a new and distinct cultivar of *Cotoneaster* plant, botanically known as *Cotoneaster* x *suecicus* and hereinafter referred to as 'Emerald Beauty'.

The new *Cotoneaster* plant is a result of a breeding program directed by the inventor at Oregon State University, Corvallis, Oreg. (US) to develop new cultivars of *Cotoneasters* that are resistant to fire blight caused by the pathogen *Erwinia amylovora*, are compact, and perform well in nursery production and landscapes.

'Emerald Beauty' originated as an open-pollinated seedling collected from *Cotoneaster* x *suecicus* 'Coral Beauty' (seed parent, unpatented) during 2011 that was pollinated by an unknown pollen parent. It was originally accessioned and evaluated as H2011-02-005. 'Emerald Beauty' was grown in containers during 2012 for observation and selected for propagation in 2013. It was propagated by stem cuttings in Corvallis, Oreg. Cuttings rooted easily with hormone treatment under mist. Clones produced from serial asexual propagation and grown in Corvallis, Oreg. have demonstrated the stability of its traits from 2013 through 2019. Replicates produced from stem cuttings were included in a glasshouse study to evaluate fire blight resistance of hybrids and parents during 2014. Plants were inoculated with a virulent strain (Ea153) of *Erwinia amylovora* by bisecting the two youngest leaves on vigorously growing shoots according to the method of Rothleutner et al. (*HortScience,* 49, 1480-1485, 2014). Plants of this accession exhibited extremely minor disease symptoms (1% shoot infection). 'Coral Beauty' had 11.1% mean shoot infection during that evaluation. 'Emerald Beauty' has not been inoculated with all isolates under all conditions but in one study with a highly virulent but extremely rare isolate (La635) 'Emerald Beauty' had a mean shoot infection of 10.4% and in that same study, 'Coral Beauty' had a mean shoot infection of 15.6%.

SUMMARY

Plants of the new *Cotoneaster* have not been observed under all possible environmental conditions. The phenotype may vary somewhat with variations in environment and cultural practices such as temperature and light intensity without any variance in genotype.

The following traits have been repeatedly observed and are determined to be unique to 'Emerald Beauty'. Collectively, these traits distinguish 'Emerald Beauty' from other available *Cotoneasters.*

1. Resistance to fire blight
2. Excellent container production performance that required pruning only at potting
3. Rapid propagation and production that progressed from rooting to shifting in as little as four weeks
4. Improved landscape aesthetics due to improved branching Compared to its female parent, *Cotoneaster* x *suecicus* 'Coral Beauty', plants of 'Emerald Beauty' are easily distinguishable based on the following traits:

1. 'Emerald Beauty' plants have a more regular growth form.
2. 'Emerald Beauty' plants have a more compact habit.
3. 'Emerald Beauty' plants have fire blight (*Erwinia amylovora*) resistance.
4. 'Emerald Beauty' plants require less pruning during production to yield salable plants.

The foregoing and other objects and features of the new variety will become more apparent from the following detailed description, which proceeds with reference to the accompanying figures.

BRIEF DESCRIPTION OF THE DRAWINGS

The accompanying photographs illustrate a new cultivar in color as nearly true as it is reasonably possible to make the same in color illustrations of this nature. The plants were grown outside in full sun in containers and in the landscape in Corvallis, Oreg., USA.

DETAILED DESCRIPTION

Figure 1:
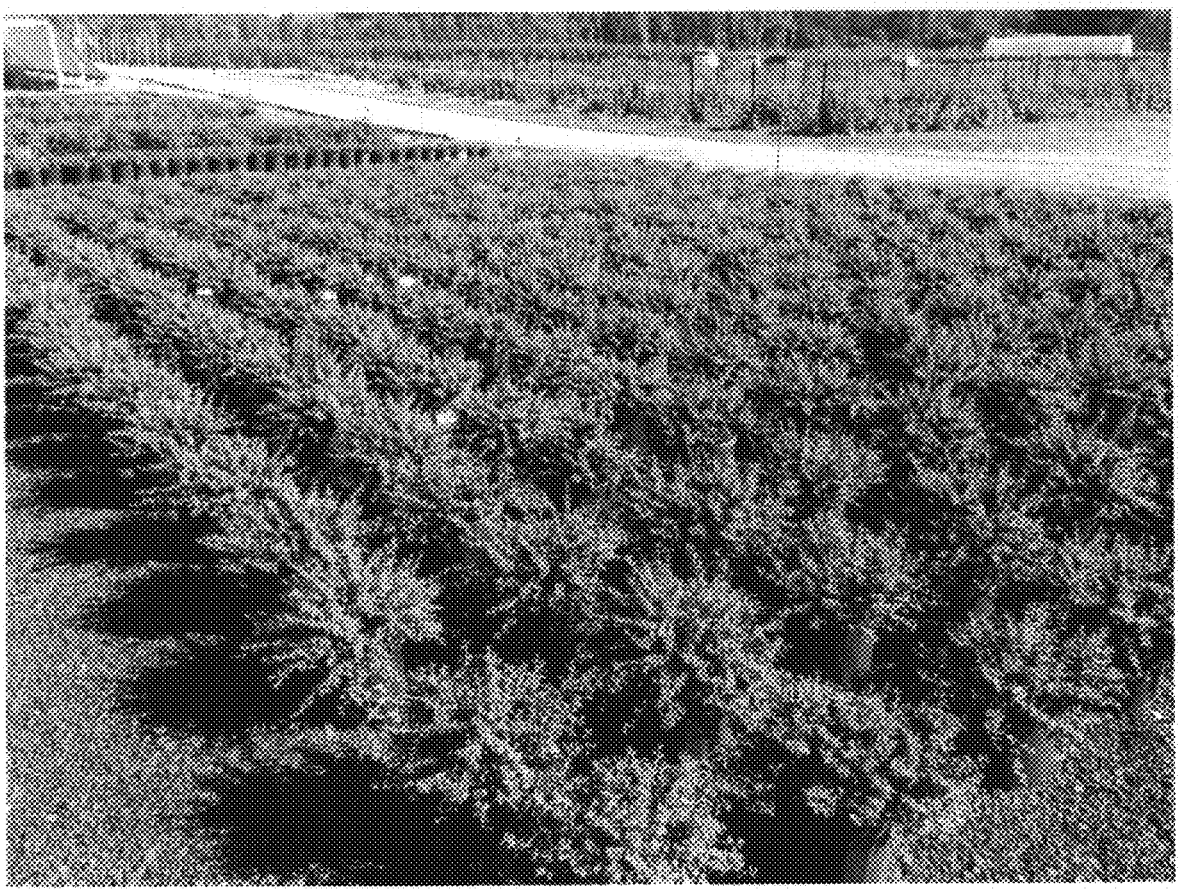
FIG. 1—Illustrates a production block of two-year old 'Emerald Beauty' plants growing in containers. The uniform, extensive branching habit of 'Emerald Beauty' is clearly visible.
Figure 2:
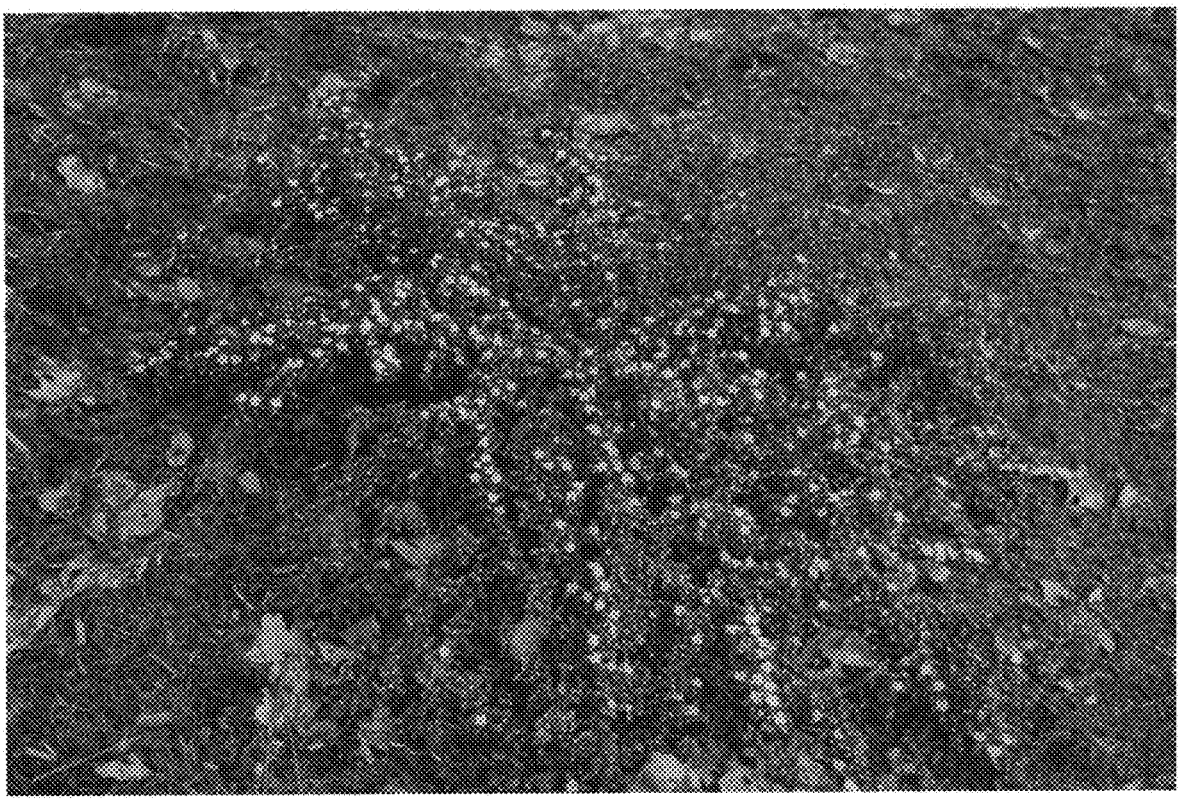
FIG. 2—Illustrates the floriferous nature of the 'Emerald Beauty' cultivar as well as its habit when left unpruned at any stage of production.
Figure 3:
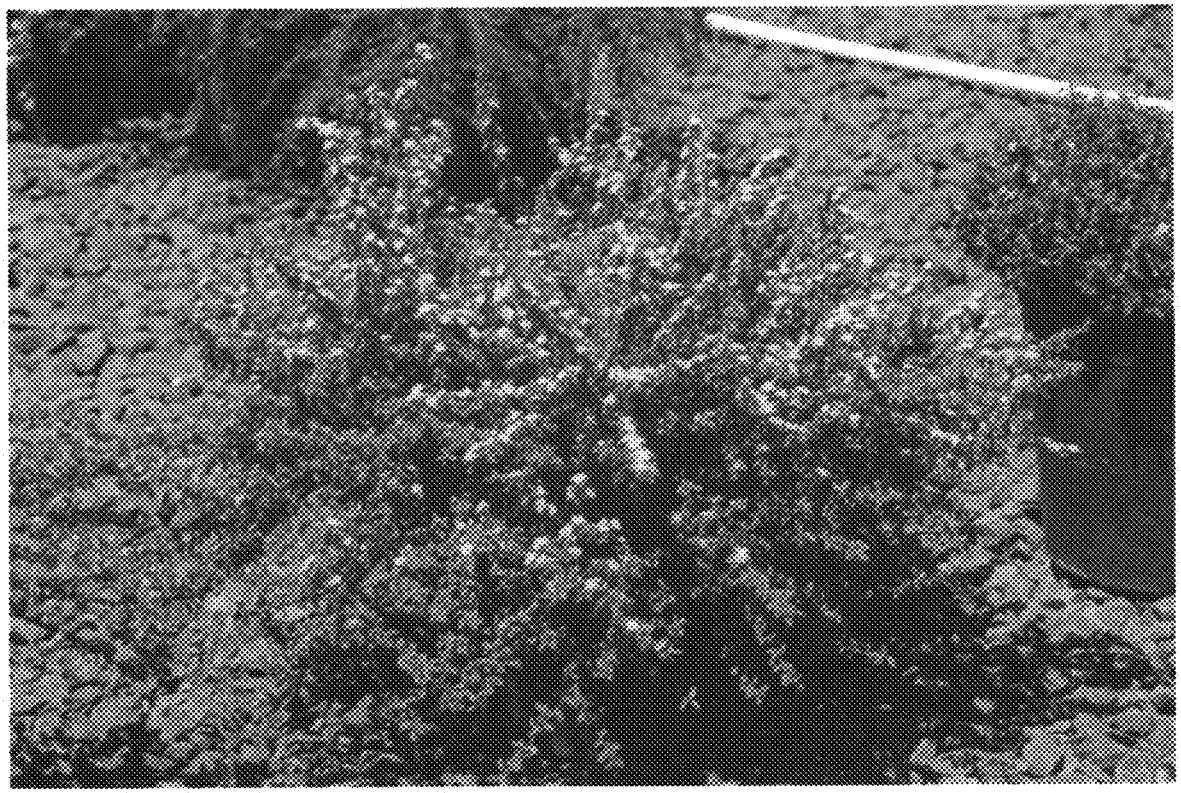
FIG. 3—Illustrates the mounding habit and flowering of 'Emerald Beauty'.
Figure 4:
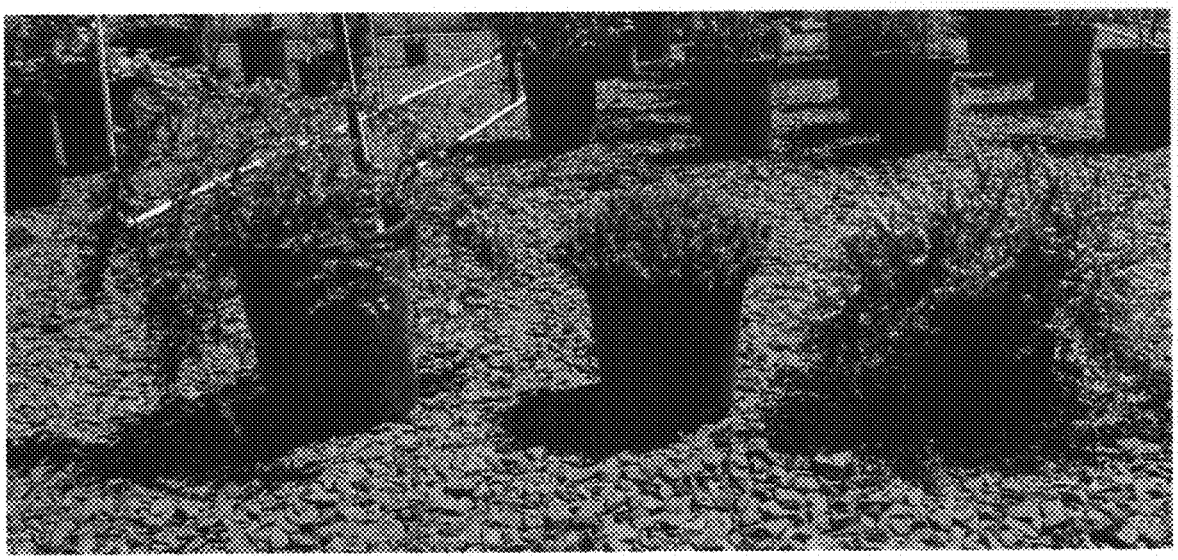
FIG. 4—Comparison of 'Coral Beauty' (left) 'Emerald Sprite' (center, U.S. Plant Pat. No. 31,719) and 'Emerald Beauty' (right) that clearly illustrates the compact nature of 'Emerald Sprite' and the improved branching and habit of 'Emerald Beauty' compared to 'Coral Beauty'; all plants in this photo were unpruned.
Figure 5:
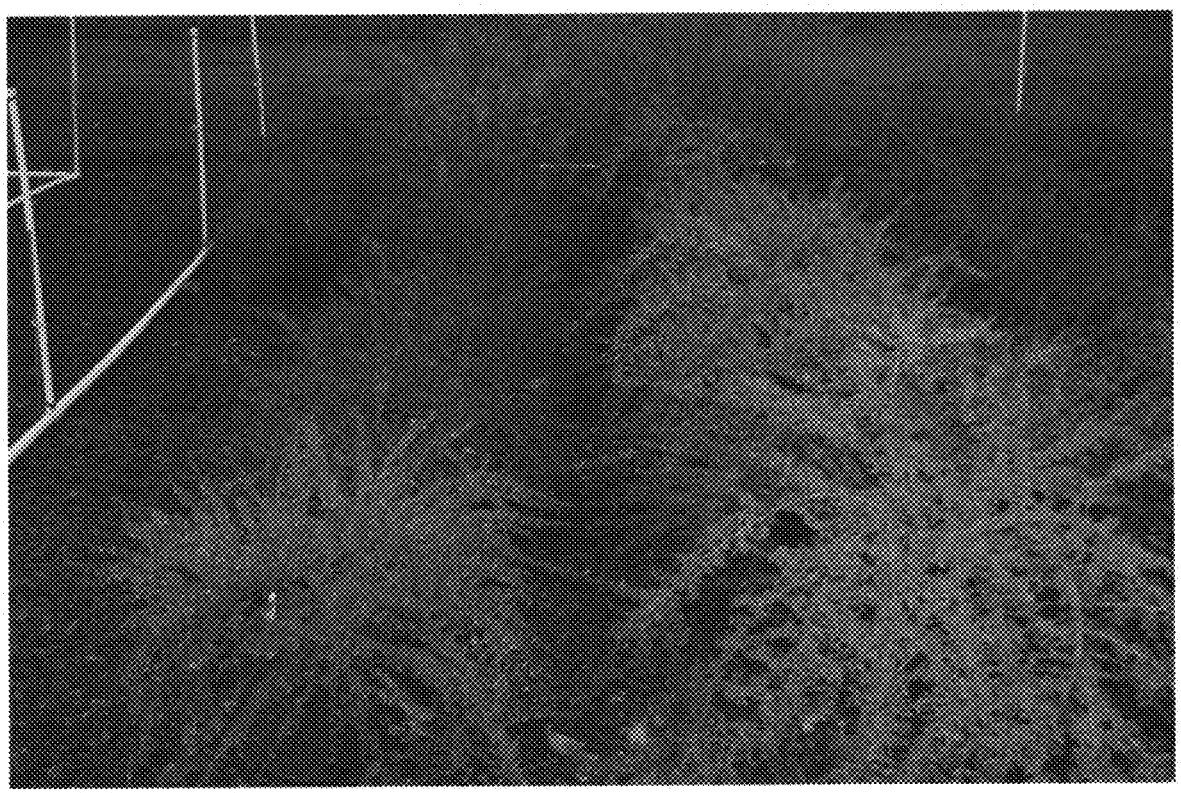
FIG. 5—Comparison of clones of 'Emerald Beauty' (left) with 'Coral Beauty' (right) during fall when plants were exhibiting fall color; all plants were unpruned.
Figure 6:
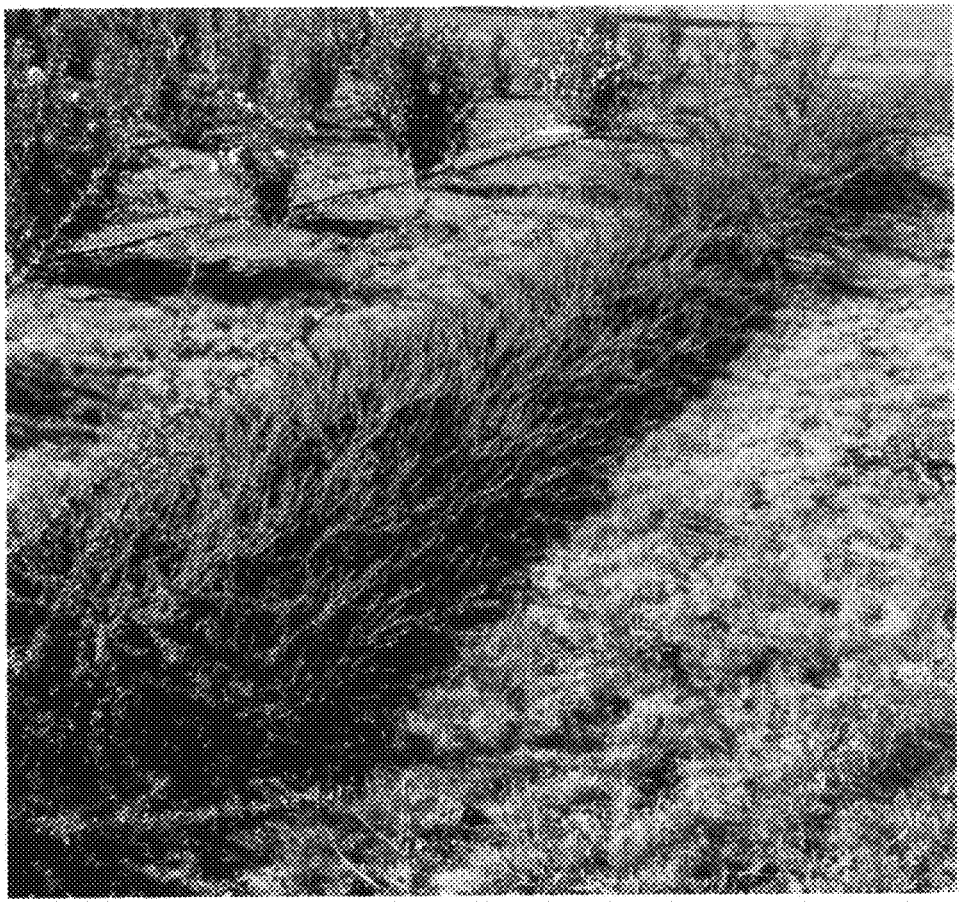
FIG. 6—Illustrates the uniform branching habit of 'Emerald Beauty' in the landscape.
Figure 7:
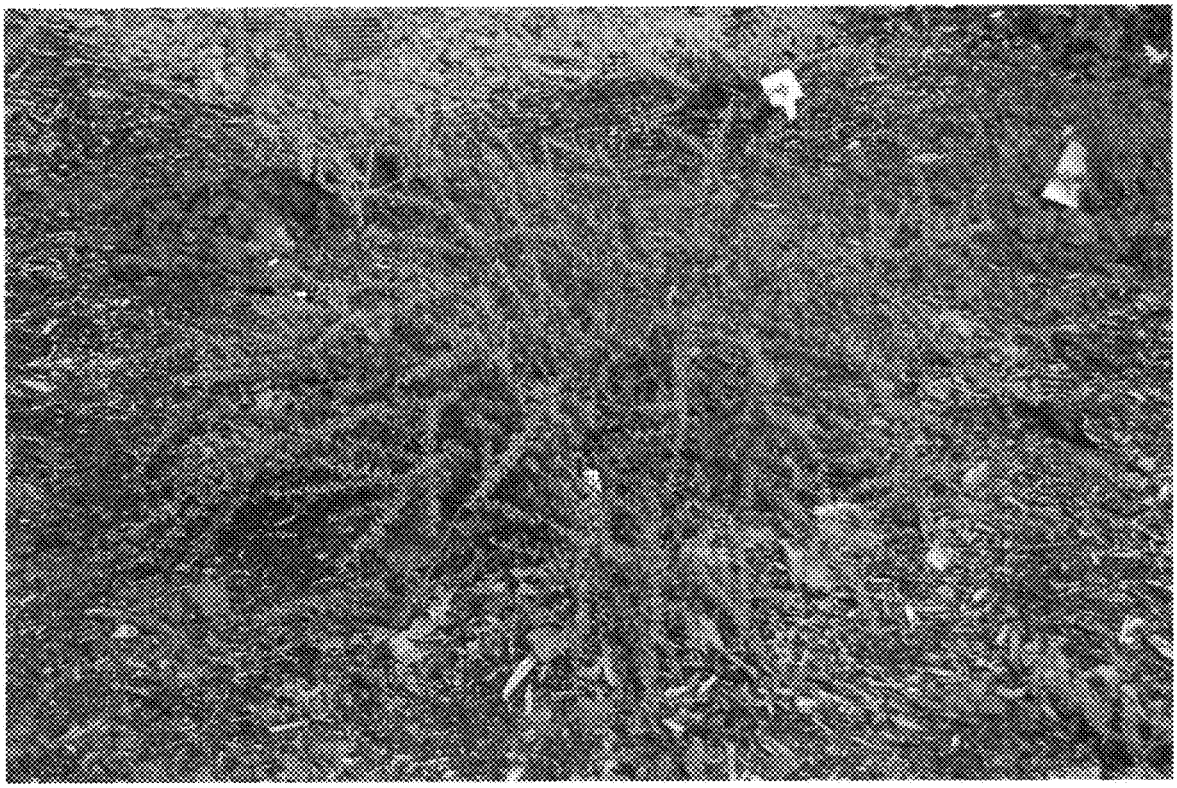
FIG. 7—Illustrates the fruit set of 'Emerald Beauty' in the landscape.
Figure 8:
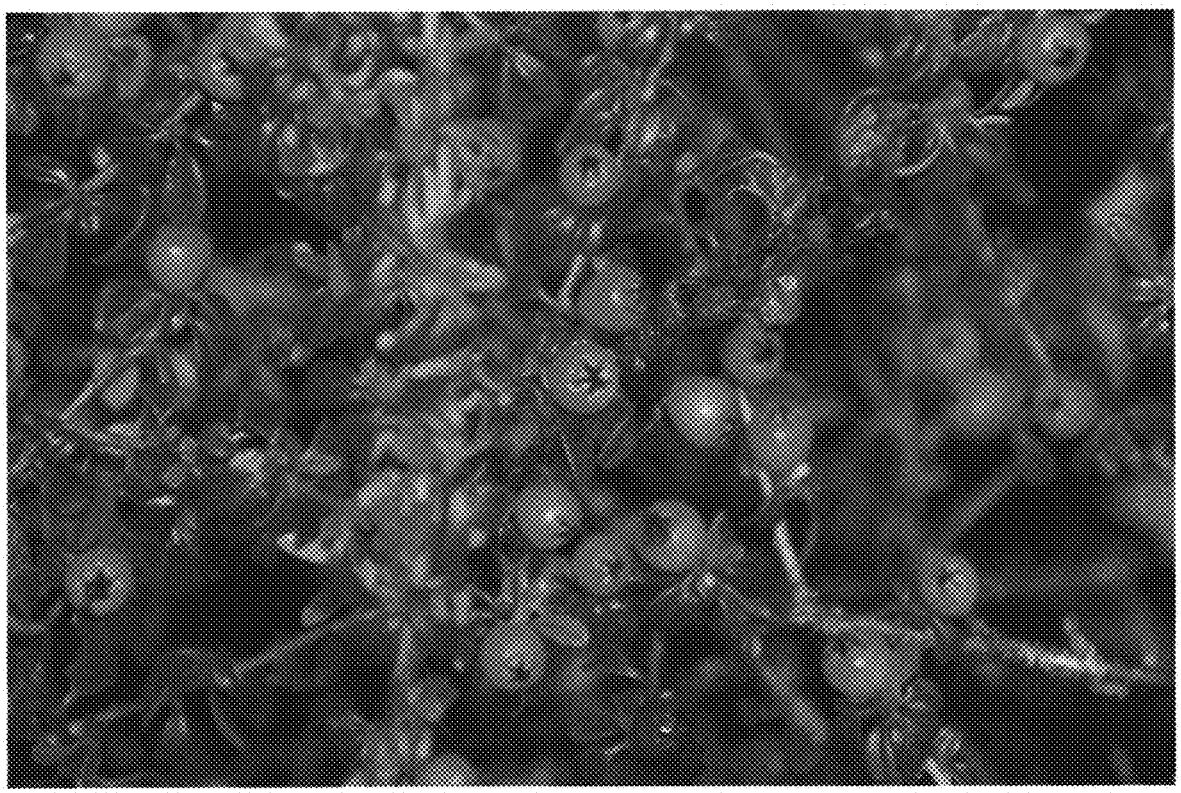
FIG. 8—Illustrates a close-up image of fruit of 'Emerald Beauty'.

The following is a detailed description while observing mature plants of the new following the rooting of stem cuttings. Such plants ranged between two and five years of age and were found to have consistent morphology with the exception of size (younger plants are smaller). Plants were observed growing outdoors in full sun in Corvallis, Oreg., USA. Color terminology is in accordance to The R.H.S. Colour Chart (fifth edition) of The Royal Horticultural Society, London, 2007.

Classification:

*Botanical name.*—*Cotoneaster* x *suecicus.*
*Common name.*—*Cotoneaster.*
*Variety name.*—'Emerald Beauty'.

Parentage: Open-pollinated seedling collected from *Cotoneaster* x *suecicus* 'Coral Beauty', which was pollinated by an unknown pollen parent — likely a self-pollination.

Plant description:

*Growth habit.*—Cushion-like to semi-rounded, stems rooting at nodes.
*Height at maturity.*—51 cm.
*Width at maturity.*—92 cm.

Stem:

*Mature stem texture.*—Glabrous.
*Mature stem color.*—Brown Group 200B and in some stems transitioning to Brown Group N200B lower on the stem where it exhibited a slightly glaucous appearance.
*Immature stem color.*—Green Group 138B.
*Length.*—33 cm.
*Diameter.*—0.3 cm.
*Internode length.*—0.3 cm.

Leaves:

*Type.*—Evergreen to semi-evergreen.
*Arrangement.*—Alternate.
*Shape.*—Elliptic, keeled.
*Veins.*—Pinnate.
*Vein color.*—Adaxial surface — Green Group N139A, Abaxial surface — Greyed-Green Group 191B.
*Mature leaf texture.*—Glabrous adaxially, light pubescent and reticulate abaxially.
*Base.*—Cuneate to nearly rounded.
*Apex.*—Mucronate.
*Margin.*—Entire.
*Mature leaf size.*—2.2 cm long×0.93 cm wide.
*Mature leaf color.*—Adaxial surface — Green Group N139A, Abaxial surface — Greyed-Green Group 191B.
*Fall color.*—Highly variable; predominating color 184A Greyed-Purple Group.
*Petiole length.*—0.46 cm.
*Petiole diameter.*—0.65 mm.
*Petiole color.*—Yellow-Green Group N144C.

Inflorescence:

*Number of flowers per inflorescence.*—Solitary or 2-5.
*Diameter.*—0.8 to 1.1 cm.
*Type.*—Solitary or corymb.
*Flowering season.*—May to June.
*Petal.*—Five petals, White Group NN155C.
*Petal shape.*—Rhombic-obdeltoid.
*Petal length.*—4.5 mm.
*Petal width.*—4 mm.
*Petal apex.*—Rounded to subacute.
*Petal margin.*—Entire.
*Petal base.*—Rounded.
*Petal surface texture.*—Glabrous abaxially and adaxially.
*Peduncle length.*—Up to 5 mm.
*Peduncle diameter.*—About 1 mm.
*Peduncle color.*—Greyed-Purple Group 183A.
*Sepal shape.*—Deltoid.
*Sepal number.*—5.
*Sepal length.*—1.3 mm.
*Sepal width.*—1.3 mm.
*Sepal apex.*—Acute.
*Sepal margin.*—Entire and ciliate-puberulent.
*Sepal surface texture.*—Pubescent adaxially, glabrous abaxially.
*Sepal color.*—Abaxial and adaxial surfaces are Yellow-Green Group N144C.

Fruit:

*Fruit*.—Obovate, 0.75-0.8 cm diameter and 0.85 cm long, sun-exposed base color is Red Group 42B with a somewhat irregular blush coloration where shaded that is Red Group 39B.

*Seeds*.—Three per fruit. Color varies from 173D Greyed-Orange Group through 173C Greyed-Orange Group to 178A Greyed-Red Group.

Propagation and production: 2.5 cm softwood terminal and subterminal cuttings treated with 1000 ppm auxin and set in 3 parts perlite: 2 part peat in a community flat under intermittent mist and bottom heat rooted >90% in 28 days. Observations indicate that plants can be propagated and produce a finished trade gallon container in approximately 9-months.

Disease and insect resistance: 1% shoot infection following inoculation with a virulent strain of *Erwinia amylovora* (Ea153), whereas its seed parent, *Cotoneaster* x *suecicus* 'Coral Beauty' had 11.1% mean shoot infection during the same evaluation.

I claim:

1. A new and distinct cultivar of *Cotoneaster* plant as illustrated and described.

* * * * *